United States Patent [19]

Murtha

[11] 4,152,362

[45] May 1, 1979

[54] HYDROALKYLATION USING A RHENIUM, NICKEL, RARE EARTH ZEOLITE

[75] Inventor: Timothy P. Murtha, Bartlesville, Okla.

[73] Assignee: Phillips Petroleum Company, Bartlesville, Okla.

[21] Appl. No.: 866,440

[22] Filed: Jan. 3, 1978

[51] Int. Cl.$^2$ ............................................. C07C 15/02
[52] U.S. Cl. ................................ 585/267; 252/455 Z; 585/268; 585/426
[58] Field of Search ........................ 260/668 B, 668 R

[56] References Cited

U.S. PATENT DOCUMENTS

| | | | |
|---|---|---|---|
| 3,760,018 | 9/1973 | Suggitt et al. | 260/668 R |
| 3,839,477 | 10/1974 | Suggitt et al. | 260/668 R |

*Primary Examiner*—Veronica O'Keefe

[57] ABSTRACT

A reaction mixture comprising an aromatic hydrocarbon and hydrogen is contacted under hydroalkylation conditions with a composition comprising at least one rhenium compound supported on a calcined, acidic, nickel and rare earth-treated crystalline zeolite.

10 Claims, No Drawings

HYDROALKYLATION USING A RHENIUM, NICKEL, RARE EARTH ZEOLITE

The invention relates to a hydroalkylation process, a composition useful as a catalyst in said process and a method for producing said composition.

Prior art catalysts in the field of hydroalkylation processes suffer from several drawbacks. Some of the deficiencies of prior art catalysts for use in hydroalkylation reactions include: (1) The use of support materials for certain catalysts which are not able to withstand the temperature employed in a typical air burn-off regeneration operation. Such regeneration operations are commonplace in the catalytic art for hydrocarbon conversions of various types and it is highly desirable that catalysts for use in hydroalkylation process be stable to such typically employed regeneration conditions. (2) Productivity is rather low as judged by the low liquid hourly space velocities (LHSV) that are utilized in the prior art. Thus a more active and more selective hydroalkylation catalyst is desired. (3) A number of the catalysts of the prior art for use in hydroalkylation reactions are prepared by very complex and time consuming processes. For example, starting with a powdered crystalline zeolite support, said support is cation exchanged, washed and then incorporated into a matrix of another material such as silica-alumina. This combination is calcined, cooled, and impregnated with certain metal salts. Finally the composite is extruded into pellets and the like. Thus it is desirable that a more simplified and less expensive process for making active and selective catalysts be found. (4) Certain catalysts of the prior art for use in hydroalkylation reactions were of fixed acidity because of the type of support material utilized. This left little variation that could be made in this important property of the hydroalkylation catalyst. It is therefore desirable that catalysts be developed in which their acidity characteristics are varied easily. (5) Certain catalysts of the prior art employ very expensive chemical components. It is desirable to develop a catalyst system that is as effective as those employing very expensive components but which employs cheaper chemicals to reduce the cost of the catalyst system. (6) Frequently hydroalkylation feed streams contain sulfur and certain hydroalkylation catalyst systems are very sensitive to the presence of sulfur in the hydrocarbon feedstream. Thus it is desirable to develop a catalyst system that is less sensitive to the presence of sulfur in the hydrocarbon feedstream as compared to certain prior art catalyst systems.

It is an object of the present invention to hydroalkylate aromatic compounds.

Another object of the present invention is to provide a method for producing a composition useful as a hydroalkylation catalyst.

Another object of the invention is a composition useful as a catalyst in hydroalkylation reactions which is regenerated by air burn-off.

Another object of the invention is a composition useful as a catalyst in hydroalkylation reactions which is more active and more selective than prior art catalysts and which is less sensitive to the presence of sulfur compounds in the feed as compared to certain prior art compositions.

Another object of the invention is a composition useful as a catalyst in hydroalkylation reactions which is simpler and less expensive to produce as compared to prior art catalysts.

Still another object of the invention is a composition useful as a catalyst in hydroalkylation reactions in which the acidity of the catalyst can be adjusted.

SUMMARY

According to the invention an aromatic hydrocarbon is contacted under hydroalkylation conditions and in the presence of hydrogen with a composition comprising at least one rhenium compound supported on a nickel and rare earth-treated crystalline zeolite support which is calcined to produce an acidic support before or after impregnating the rhenium compound on the support. Such a composition, when used as a catalyst, can be regenerated by air burn-off and is a highly active and selective catalyst. Further, such a catalyst system is believed to be less sensitive to sulfur poisoning as compared to some other systems.

Further according to the invention a composition comprises at least one rhenium compound supported on a calcined, acidic, nickel and rare earth-treated crystalline zeolite.

Further according to the invention the above composition is prepared by contacting a crystalline zeolite with an aqueous cation exchange solution comprising rare earth metal, nickel and ammonium compounds; removing the thus cation exchanged zeolite from said solution and washing said zeolite with water to remove excess ions; calcining the thus washed zeolite; cooling the thus calcined zeolite; and impregnating said cation exchanged zeolite before or after the calcining step with a solution comprising at least one rhenium compound in a suitable solvent and then removing said solvent by evaporation. The acidity of the above composition is easily adjusted by varying the conditions under which the cation exchange step is carried out, such as, for example, adjusting the concentration of an ammonium compound in the cation exchange solution.

DETAILED DESCRIPTION OF THE INVENTION

The composition of the instant invention can be briefly described as a crystalline zeolite which has been cation exchanged with rare earth, nickel and ammonium compounds followed by a calcination step and a rhenium compound which has been impregnated on the cation exchanged zeolite, either before or after the calcination step, to give the final composition. Although not absolutely necessary, it is preferred that the above composition be treated with hydrogen prior to contact of the composition with the aromatic hydrocarbon feed in the hydroalkylation process, because such pretreatment provides improved results.

The compositions of the instant invention are useful as catalysts and to some extent solve or obviate each of the above-mentioned deficiencies of the prior art catalysts. For example, the supports utilized for the compositions of the instant invention are stable to regeneration conditions utilized under typical air burn-off operations; they appear to operate at higher levels of productivity in that they show a higher degree of activity and selectivity than certain of the prior art catalysts; the process of making the compositions of the instant invention is simple and straightforward and the compositions thus obtained are less expensive than those of the prior art which utilize very complex steps in their preparation or chemicals more expensive than compounds of rhenium;

and the compositions of the instant invention can be made with a high degree of flexibility in the degree of acidity simply by adjusting the cation exchange conditions on the crystalline zeolite support utilized for the compositions of this invention.

The support material for the composition employed in the instant invention is a crystalline zeolite which has been treated under cation exchange conditions with a mixture of rare earth, nickel and ammonium compounds such that the cation metal content of the support is partially exchanged. Generally the cationic metal is an alkali metal or an alkaline earth metal which is sufficiently removed by cation exchange. In those instances where the cationic metal is an alkali metal, the remaining alkali metal content after the cation exchange step will generally be within the range of about 0.01 to about 2 percent by weight of said zeolite; however, based upon the runs carried out in accordance with the invention and reported herein it is believed that better results can be obtained when the alkali metal content of the cation exchanged zeolite is within the range of about 0.1 to 1 percent by weight of said zeolite. Some of the more commonly employed crystalline zeolites which are suitable for use in accordance with the present invention are the Type X, Type L and Type Y crystalline zeolites and other crystalline zeolites havng a pore diameter within the range of about 7 to about 12 angstroms which are sometimes called molecular sieves because of their essentially uniform pore diameter. Some suitable Type X, Type Y and Type L synthetic crystalline zeolites are described for example in U.S. Pat. Nos. 2,882,244, 3,013,982, 3,130,007, 3,200,082 and 3,236,762. Such materials are presently commercially available as for example zeolites SK-40 (Type Y), SK-45 (Type L), and 13X (Type X) from the Linde Division of Union Carbide Corporation, New York, New York.

The alkali metal form of the crystalline zeolites usually comprises sodium as the alkali metal and such zeolites are treated under cation exchange conditions with a mixture of at least one rare earth metal compound, nickel compound and ammonium compound in accordance with the present invention in order to provide a suitable support material for use in the preparation of he compositions of the invention. Generally an aqueous cationic exchange solution is used; however, any suitable diluent or mixtures of two or more diluents can be used. Water is preferred because it is readily available and of course inexpensive. Ion exchange procedures are sufficiently well known to permit one skilled in the art to practice the invention. In preparing the crystalline zeolite support of the present invention the amount of diluent employed in preparing the ionic exchange solution is not believed to be critical and can be selected over a broad range. Frequently the amount of diluent employed is within the range of about 1 to about 50 milliliters of diluent per gram of ion exchange compounds. In the Examples described herein the amount of diluent employed was approximately 4 liters per 700 grams of ion exchange compounds or about 5.7 milliliters per gram of ion exchange compounds.

As known by those skilled in the art it is frequently desirable to treat the crystalline zeolite with air at room temperature (22° to 25° C.) and at normal humidity (30 to 70%) for 24 to 48 hours prior to the cation exchange procedure to partially hydrate the zeolite which helps to protect the zeolite from thermal shock during the cation exchange step.

It is contemplated that any of the readily available rare earth metal compounds can be employed in the cation exchange solution. Generally, the compounds used are those in which the rare earth metal-containing ion is present in the cationic state. Representative rare earth metal compounds include nitrates, bromides, acetates, chlorides, iodides, sulfates and mixtures of any two or more thereof of one or more of the rare earth metals including cerium, lanthanum, praseodymium, neodymium, samarium, europium, gadolinium, terbium, dysprosium, holmium, erbium, thulium, ytterbium, and lutetium. Compounds of the rare earths named above may be employed singly, however, it is often convenient to employ mixtures of two or more of the rare earths as these are commercially available. For example, mixtures of rare earth metal compounds such as the chlorides of lanthanum, cerium, praseodymium, neodymium, samarium and gadolinium are available commercially at a relatively low cost and may be effectively employed.

As noted above, the zeolite material is cation exchanged with a mixture of rare earth metal compounds, nickel compounds and ammonium compounds according to the instant invention. Any convenient ammonium compound may be employed although the chloride is preferred because it is inexpensive and readily available. The weight ratio of ammonium compounds to nickel compounds and rare earth compounds in the exchange solution can be selected over a broad range. Generally the weight ratio of ammonium compounds to nickel compounds and rare earth compounds combined is within the range of about 0.05:1 to about 20:1, although based upon the data contained herein it is believed that values in the range of about 0.2:1 to about 5:1 can be used with better results. The concentration of rare earth compounds in the exchange solution can be varied over a wide range and exchange conditions can be adjusted accordingly such that the rare earth content of the ion exchanged crystalline zeolite can be selected over a broad range. Generally, the content of the ion exchanged zeolite in terms of the rare earth elements is from about 2 to about 25 weight percent of said zeolite. Based upon the runs described herein it is believed that the rare earth content of the ion exchanged zeolite can be within the range of from 5 to 20 weight percent of said zeolite. Good results were obtained employing a rare earth content of about 10 percent by weight of said zeolite. As noted above, the alkali metal content, for example sodium, of the ion exchanged zeolite is partially removed by the ion exchange step and the alkali metal is generally within the range of from about 0.01 to about 2 percent by weight of said zeolite; however, based upon the runs described herein it is believed that good results can be obtained employing an alkali metal content within the range of from about 0.1 to about 1 percent by weight of said zeolite.

The nickel compounds which will be employed in admixture with the above-named rare earth metal compounds and ammonium compounds are those wherein the nickel ion is present in the cationic state. Some suitable compounds representative of the nickel compounds which can be used in the invention include the nitrates, bromides, acetates, chlorides, iodides, sulfates and mixtures of any two or more thereof.

The nickel content in the ion exchanged zeolite can also be selected over a broad range. Generally the ion exchanged zeolite will comprise from about 0.01 to about 15 weight percent nickel based on weight of the zeolite, although the runs carried out in accordance with the invention and described herein support the belief that good results can be obtained employing a nickel content within the range of from about 1 to about 8 percent by weight based on weight of the zeolite.

The procedure whereby the zeolite is treated with solutions of rare earth metal compounds, nickel compounds and ammonium compounds to replace a portion of the alkali metal content of the zeolite is a cation exchange process which can be carried out in a batch or continuous fashion. As an example of a suitable process, for illustration, the exchange process can be carried out on a continuous basis under the following typical conditions. A fixed bed of the zeolite material can be treated with an aqueous solution of the rare earth metal compounds, nickel compounds and ammonium compounds at a temperature in the range of about 90 to about 110° C. under conditions such that from about 0.1 to about 0.5 of the volume of the aqueous solution per volume of zeolite is in contact with said zeolite per hour or, in other words, an LHSV ranging from about 0.1 to about 0.5 is employed in the exchange process. Under these conditions, the exchange process can be completed in 48 hours or less to achieve the desired level of rare earth, nickel and ammonium ions in the zeolite. The exchanged zeolite can then be washed with water to free it of excess ions from the exchange step. The wash water can be removed by drying the zeolite at a temperature in the range of about 100° C. to about 300° C. prior to calcination. The catalyst can be calcined before impregnation with the rhenium compound or the impregnation can be carried out prior to the calcination step. In either case, the calcination can be carried out by slowly heating the zeolite to a temperature within a range of about 100° to 200° C. and slowly increasing the temperature to a temperature within the range of about 450° to about 550° C. in order to calcine the zeolite and convert the ammonium cations to the hydrogen form. Usually, the calcination is conducted until a constant weight for the zeolitic material is obtained, generally this takes from about 2 to about 10 hours. The calcined zeolite can then be cooled in ambient air, i.e., under conditions of normal humidity.

The support employed in the invention is impregnated with a solution of at least one rhenium compound followed by evaporation of the solvent used in the impregnation step. Evaporation of the solvent can be conducted under vacuum if desired. Suitable solvents include water, alcohols, and ketones. Some of the various rhenium compounds that can be employed in the impregnation step are: perrhenic acid — $HReO_4$, ammonium perrhenate — $NH_4ReO_4$, potassium hexachlororhenate — $K_2ReCl_6$, potassium perrhenate — $KReO_4$, rhenium carbonyl — $Re_2(CO)_{10}$, rhenium heptoxide — $Re_2O_7$, rhenium pentachloride — $ReCl_5$, rhenium trichloride — $ReCl_3$, rhenium trioxide — $ReO_3$, sodium perrhenate — $NaReO_4$, and mixtures of any two or more thereof. For obvious reasons of economy the impregnation is generally carried out under what may be called "total impregnation" whereby the entire solids in the solutions used in the impregnation are left on the catalyst support and the liquid solvent for the rhenium compound or compounds is simply removed by evaporation; however, most any impregnation procedure can be employed if desired. The amount of solvent employed should be sufficient to properly distribute the rhenium compound on the support as known in the art.

The rhenium content in the final catalyst composition can be selected over a broad range. Generally the rhenium content is within a range of 0.01 to about 1 percent by weight of the catalyst although based upon the runs described herein it is believed that good results can be obtained employing a rhenium content within the range of from about 0.05 to 0.25 percent by weight of the catalyst.

The catalyst of the invention can be employed for the hydroalkylation of aromatic hydrocarbons to produce cycloalkyl aromatic hydrocarbons. Some of the feedstocks which are suitable for use in the present invention are aromatic compounds, i.e., monocyclic aromatic hydrocarbons and alkyl-substituted monocyclic aromatic hydrocarbons; however, polycyclic aromatic compounds can be employed if desired. Generally the aromatic feedstocks suitable for use in the invention have carbon atoms within the range of 6 to about 24 carbon atoms. Some specific examples of these are benzene, toluene, xylenes, naphthalene, anthracene, and mixtures of any two or more thereof. While in most hydroalkylation reactions it is necessary that the aromatic hydrocarbon feedstocks be essentially free of sulfur-containing compounds and other known poisons for hydrogenation catalysts, it is believed that the rhenium-based compositions of the present invention are less sensitive to the presence of sulfur-containing compounds as compared to certain other hydroalkylation catalyst systems. Also, it is believed that a small amount of water, e.g., 20–50 ppm, in the feedstock is beneficial for maintaining catalyst activity over an extended period, e.g., several days.

The invention is particularly valuable for the conversion of benzene to cyclohexylbenzene. Cyclohexylbenzene is known as a valuable solvent and chemical intermediate. It can be converted in high yield to phenol and cyclohexanone by autooxidation with subsequent acid treatment. It is also useful as an intermediate in the production of cyclohexene which in turn can be utilized for the production of adipic acid and caprolactam.

The aromatic hydrocarbon feedstock is fed to the catalyst in a reaction zone operable under a wide range of conditions. The feedstock liquid hourly space velocity (LHSV), reaction temperature and pressure, and the hydrogen feed rate are not particularly critical; however, the liquid hourly space velocity (LHSV) is generally within the range of about 1 to about 100, the reaction pressure is generally within the range of about 690 to about 13,800 kPa (about 100 to about 2,000 psig), the hydrogen feed rate is generally within the range of about 0.2 to about 1 mole per mole of aromatic hydrocarbon feedstock per hour, and the reaction temperature is generally within the range of about 100° to about 250° C. Based upon the runs described herein good results can be obtained employing a liquid hourly space velocity (LHSV) within the range of about 5 to about 25, a reaction pressure within the range of about 1,380 to about 6,900 kPa (about 200 to about 1,000 psig), a hydrogen feed rate within the range of about 0.2 to about 1 mole per mole of aromatic hydrocarbon feed per hour, and a reaction temperature within the range of about 140° to about 200° C.

The hydroalkylation reaction is conveniently carried out by having the above described catalyst in a fixed bed reactor and then contacting said catalyst with the aromatic hydrocarbon feed and hydrogen in an upflow or downflow arrangement. It is also possible to employ a countercurrent flow of hydrogen and the aromatic hydrocarbon feed over the catalyst in the reaction zone. It is also possible to carry out the hydroalkylation reaction under batch conditions although a batch process is less preferred, because it is normally more expensive to operate and initial equipment costs are higher based upon the same size process.

Although a fixed bed reactor is mentioned above, most any type of reaction zone can be used as the particular type of reaction zone is not believed to be a critical parameter of the invention.

The reaction mixture from the reaction zone can usually be conveniently separated into the desired components by simple fractional distillation, and recycle of the unreacted feedstock and unreacted hydrogen can be accomplished as desired. The hydroalkylation products can be further purified as desired after separation from unreacted feedstock.

It is generally desirable to pretreat the catalyst with hydrogen gas prior to contacting the catalyst with the aromatic hydrocarbon in order to prereduce the catalyst. Such a prereduction step is generally carried out for a period time ranging from about 10 minutes to about 2 hours, at a temperature within the range of from about 150° C. to about 250° C., at a pressure within the range of about 690 kPa (100 psig) to about 6,900 kPa (1,000 psig), and at a hydrogen flow rate within a range of from about 0.01 to about 10 liters per minute. In the hydroalkylation runs of the examples hereinafter described, the catalyst in the reactor was first reduced at about 170° C. for 15 minutes under 3,450 kPa (500 psig) hydrogen at a hydrogen flow rate of 0.32 liter per minute before benzene was introduced to the reactor. Hydrogen pressure during the hydroalkylation process was maintained at 3,450 kPa (500 psig) and at a flow rate of about 0.32 liter per minute.

The catalyst of the instant invention can be regenerated utilizing a procedure which typically involves heating the catalyst in the presence of air at a temperature within the range of about 400° to about 500° C. followed by cooling under a stream of nitrogen to a temperature near that to be utilized in the hydroalkylation reaction and then introduction of hydrogen near the reaction temperature to reduce (reactivate) the catalyst under conditions described above.

EXAMPLE I

A catalyst (No. 1) was prepared according to the instant invention in the following manner: 350 g of a Type X crystalline zeolite (Davison 13X molecular sieve, grade 544, 8-12 mesh) was treated at ambient temperature (22° to 25° C.) under a current of flowing air of ambient humidity (30 to 70%) over a two day period to partially hydrate the catalyst in order to avoid a thermal shock of the crystalline zeolite beads during the cation exchange step. After the treatment in air the zeolite material weighed 424 g. The zeolite material was placed in a tubular glass reactor equipped with heating means and means for entrance and exit of the cation exchange solutions. An aqueous cation exchange solution of 400 g of ammonium chloride, 100 g of rare earth chlorides, and 200 g of nickel chloride hexahydrate in 4 liters of deionized water was prepared. Said rare earth chlorides were utilized as a mixture obtained from the American Potash Corporation, having the following composition: $MCl_3.6H_2O$ wherein M equals lanthanum 23%, cerium 43.5%, praseodymium 5.4%, neodymium 17.9%, samarium 1.9%, gadolinium 0.6%, and others 0.2%. The crystalline zeolite material was first wetted with a portion of the above solution and then charged to the tubular glass reactor and the remainder of the aqueous solution was then pumped over the crystalline zeolite at a rate of about 142 ml per hour. The temperature in the cation exchange zone was about 95° C. An additional 2,835 ml of the cation exchange solution was prepared having the same concentration of ammonium chloride, nickel chloride and rare earth chlorides as previously described and was also pumped over the crystalline zeolite material. After all the solution had been pumped through the crystalline zeolite bed, the zeolite was cooled, filtered and washed 6 times with 500 ml portions of water and then allowed to dry in ambient air. The cation-exchanged zelite weighed 512 g. A portion (73.1 g) of the cation-exchanged crystalline zeolite was then treated with a solution of 0.0780 g of rhenium trichloride in about 80 ml of absolute methanol under total impregnation conditions. The ethanol was removed under reduced pressure in a rotary evaporator and the catalyst was treated with ethanol a second time and dried again on the evaporator to yield 63.2 g of impregnated zeolite material. About one-half (32.6 g) of the impregnated zeolite was calcined by heating the material to about 93° C. and maintaining the zeolite at that temperature overnight and then increasing the temperature to 504° C. over a period of about 7.5 hours. The calcined material was allowed to cool and then placed in an air tight container prior to use in benzene hydroalkylation runs. The catalyst thus prepared contained 0.10 wt. % rhenium, an estimated 4.6% nickel, 9.5% rare earths and 0.6% sodium by weight.

The catalyst described above was utilized in the hydroalkylation of benzene. In these hydroalkylation runs, a small tubular reactor equipped for continuous reaction operation was charged with 11.6 g (15 ml) of catalyst No. 1 described above. The catalyst was prereduced at 170° C. under 3,450 kPa (500 psig) hydrogen pressure at a hydrogen flow rate of 0.32 liter per minute for a time period of 15 minutes. During each benzene hydroalkylation run, the hydrogen pressure was maintained at 3,450 kPa (500 psig) and at a flow rate of 0.32 liter per minute of hydrogen. The benzene feed was passed to the tubular reactor at a liquid hourly space velocity (LHSV) of 20. The effluent from the tubular reactor was analyzed by gas-liquid phase chromatography in order to determine the extent of benzene conversion and the selectivity to cyclohexylbenzene and other products of the reaction. Each run was made using the same catalyst, but in some instance (as indicated) the catalyst was regenerated prior to the next run. Other reaction conditions and results obtained in the hydroalkylation runs are shown below in Table I.

TABLE I

| | | | (Runs using catalyst No. 1) | | | | | |
|---|---|---|---|---|---|---|---|---|
| Run No. | Temp. °C. | Benzene Conv. % | Selectivity, Wt. % | | | | | Wt. Ratio CHB/CH |
| | | | $CH^{(a)}$ | $C_{12}H_{22}^{(b)}$ | $MCPB^{(c)}$ | $CHB^{(d)}$ | $Heavies^{(e)}$ | |
| 1 | 180 | 10.5 | 6.55 | 0.10 | 1.72 | 83.6 | 7.6 | 12.7 |
| 2 | 172 | 8.0 | 7.77 | tr. | 1.24 | 84.9 | 6.1 | 10.9 |
| 3$^{(f)}$ | 150 | 8.2 | 10.4 | 0.13 | 0.66 | 82.4 | 6.3 | 7.9 |

TABLE I-continued (Runs using catalyst No. 1)

| Run No. | Temp. °C. | Benzene Conv. % | Selectivity, Wt. % | | | | | Wt. Ratio CHB/CH |
|---|---|---|---|---|---|---|---|---|
| | | | CH[a] | C$_{12}$H$_{22}$[b] | MCPB[c] | CHB[d] | Heavies[e] | |
| 4[g] | 150 | 9.2 | 8.4 | 0.12 | 0.50 | 82.1 | 8.9 | 9.8 |

[a]CH — cyclohexane.
[b]C$_{12}$H$_{22}$ Compounds of the indicated general formula including bicyclohexyl.
[c]MCPB — Methylcyclopentylbenzene.
[d]CHB — Cyclohexylbenzene.
[e]Heavies — Mixture of compounds greater in molecular weight than C$_{12}$H$_{22}$.
[f]Run made after catalyst was regenerated by heating to 500°-500° C. in flowing air at atmospheric pressure for about three hours. Catalyst was cooled under flowing nitrogen and then reduced in the presence of benzene feed.
[g]Run made after second catalyst regeneration in essentially the same manner as in (f).

The results show that catalyst No. 1 is effective to hydroalkylate an aromatic hydrocarbon, such as benzene, under the conditions employed. Run 1 provided the best results by showing both the highest benzene conversion and the highest CHB/CH weight ratio.

EXAMPLE II

Another catalyst (No. 2) was prepared according to the instant invention. Catalyst No. 2 utilized 73 g of a Type X mol sieve (Davison 13X) which had been treated under cation exchange conditions in essentially the same manner as that described for the preparation of catalyst No. 1 of Example I above. Thus, the same concentrations of ammonium chloride, rare earth chlorides and nickel chloride hexahydrate were utilized in the cation exchange step as described for the preparation of catalyst 1. The 73 g sample of the cation-exchanged crystalline zeolite was impregnated with a solution of 0.0515 of perrhenic acid (HReO$_4$) in about 80 ml of absolute ethanol. The ethanol was removed on a rotary evaporator and the catalyst was then treated with ethanol a second time and dried as before on the rotary evaporator to give 66 g of catalyst material. One-half of the treated catalyst was calcined by first raising the temperature from room temperature to 193° C. overnight and then increasing the temperature slowly to 502° C. over about 7.75 hours. The catalyst was allowed to cool in air and then placed in an air tight container. The catalyst now weighed 24.8 g. The contents of rhenium, nickel, rare earths and sodium were essentially the same as that described for catalyst No. 1 above.

Catalyst No. 2 was utilized in the hydroalkylation of benzene in several runs. In these hydroalkylation runs, a small tubular reactor equipped for continuous reaction operation was charged with 11.1 g (15 ml) of catalyst No. 2. The catalyst was prereduced at 170° C. under 3,450 kPa (500 psig) hydrogen at a flow rate of 0.32 liter per minute for a period of 15 minutes. During each benzene hydroalkylation run, the hydrogen pressure was maintained at 3,450 kPa (500 psig) and at a flow rate of 0.32 liter per minute of hydrogen. Other reaction conditions and the results obtained in the hydroalkylation runs are shown below in Table II. As in earlier runs described in Example I, the tubular reactor effluent was analyzed by gas-liquid phase chromatography (GLC) to determine the extent of benzene conversion and the selectivity to cyclohexylbenzene and other products.

TABLE II (Runs using catalyst No. 2)

| Run No. | Temp. ° | Benzene LHSV | Conv % | Selectivity, Wt. % | | | | | Wt. Ratio CHB/CH |
|---|---|---|---|---|---|---|---|---|---|
| | | | | CH | C$_{12}$H$_{22}$ | MCPB | CHB | Heavies | |
| 5 | 172 | 20 | 6.5 | 7.23 | tr. | 1.02 | 85.2 | 6.6 | 11.8 |
| 6 | 151 | 10 | 9.6 | 8.0 | 0.10 | 0.64 | 83.3 | 8.1 | 10.4 |
| 7[a] | 153 | 20 | 8.9 | 9.1 | 0.04 | 0.74 | 81.4 | 8.6 | 8.9 |

[a]Run made after catalyst was regenerated in essentially the same manner as in Run No. 3 of Table I.

The results show that catalyst No. 2 was an effective benzene hydroalkylation catalyst under the conditions employed.

EXAMPLE III

Catalyst No. 3 was prepared in essentially the same manner as that described for catalyst No. 2 of Example II. This catalyst was utilized in benzene hydroalkylation runs which extended over many days. These runs, which included a number of regeneration cycles, demonstrated the extended life capabilities of the catalyst of this invention. In addition, preferred conditions for prereduction of the catalyst prior to hydroalkylation and preferred levels of water in the benzene feed to the hydroalkylation zone were determined. Run No. 8 of this example ran for 453 hours and produced about 20 pounds of cyclohexylbenzene while run No. 9 ran for 741 hours and produced 33 pounds of cyclohexylbenzene. This latter result was obtained with 11 g of 0.1 wt. % rhenium catalyst, which indicated a productivity of approximately 1,400,000 g of cyclohexylbenzene per gram of rhenium in the catalyst.

In the runs of this example it was desirable to maintain benzene conversion at about 10 wt. % since the objective was to produce a large quantity of cyclohexylbenzene in a short time. Generally the reaction was initiated at 155°-165° C. and as the catalyst became less active the temperature was increased gradually to maintain the benzene conversion near the 10% level. The upper limit of the temperature was at about 180°-185° C. This upper limit was determined by the amount of isomers in the cyclohexylbenzene product. Thus, it was desirable to maintain the isomer content below about 2% by weight. Lower reaction temperatures reduced the isomer concentration but increased cyclohexane production and lowered benzene conversion. The results of the runs of this example are presented below in Table III. The values reported in Table III below were obtained from samples taken during the cycle indicated and are considered representative of the products produced employing the reaction conditions shown.

TABLE III (Runs using catalyst No. 3)

| Run No. | Cycle No. | Time[a] hr | Benzene Temp. °C | LHSV | Conv. % | Selectivity, Wt. % CH | $C_{12}H_{22}$ | MCPB | CHB | Heavies | Wt. Ratio CHB/CH |
|---|---|---|---|---|---|---|---|---|---|---|---|
| 8 | 1 | 8 | 148 | 15 | 9.9 | 25.8 | 0.50 | 0.71 | 64.2 | 8.78 | 2.5 |
|  | 2 | 72 | 158 | 14 | 10.2 | 18.8 | 0.39 | 0.98 | 71.0 | 8.84 | 3.8 |
|  |  |  | 178 | 17 | 10.3 | 8.6 | 0.80 | 1.79 | 80.8 | 8.06 | 9.4 |
|  | 3 | 296 | 155 | 14 | 10.6 | 14.4 | 0.38 | 1.22 | 75.7 | 7.92 | 5.2 |
|  |  |  | 177 | 15 | 10.2 | 15.1 | 0.20 | 1.27 | 74.1 | 9.22 | 4.9 |
|  | 4 | 77 | 175 | 15 | 12.3 | 13.3 | 0.24 | 1.30 | 77.3 | 7.80 | 5.8 |
|  | ⊥ |  | 177 | 15 | 10.9 | 16.5 | 0.37 | 1.10 | 70.0 | 12.0 | 4.2 |
| 9 | 1 | 37 | 173 | 20 | 7.6 | 12.2 | 0.40 | 1.45 | 72.7 | 13.0 | 5.9 |
|  | 2 | 114 | 182 | 20 | 8.0 | 6.1 | 0.62 | 1.75 | 80.0 | 10.2 | 13.0 |
|  | 3 | 252 | 172 | 20 | 11.7 | 10.1 | 0.17 | 1.03 | 80.9 | 8.6 | 8.0 |
|  |  |  | 174 | 20 | 9.4 | 8.0 | 0.21 | 1.06 | 80.1 | 10.6 | 10.0 |
|  | 4 | 146 | 166 | 20 | 10.7 | 7.9 | 0.37 | 0.93 | 80.0 | 10.4 | 10.1 |
|  |  |  | 163 | 20 | 8.9 | 6.3 | 0.45 | 1.35 | 80.4 | 11.2 | 12.7 |
|  | 5 | 192 | 178 | 20 | 9.7 | 5.5 | 0.10 | 1.03 | 83.9 | 10.2 | 15.0 |

[a]Time that the catalyst was active after each regeneration.

The catalyst in run No. 8 was replaced after 453 hours (19 days) because of somewhat erratic results in terms of cyclohexylbenzene selectivity and short lived catalyst activity. A portion of the same catalyst material was charged to the reactor for run No. 9 but similar problems are noted in the first two cycles of run No. 9 as had been observed in run No. 8. It had been noted that it was necessary to keep the reaction temperature relatively high during the initial portion of these runs to maintain catalyst activity at an acceptable level. This observation indicated that the catalyst was not being sufficiently reduced during the prereduction step in order to provide suitable activity of the catalyst. This effect was examined in detail during several cycles of run No. 9 and these results are presented in Table IV below. Thus, after regeneration by burn-off of the catalyst, the catalyst was reduced for 0, 0.7 and 1.5 hours respectively. In each instance it was found that the initial reaction temperature for high benzene conversion was lower as the prereduction period was lengthened. This indicated that catalyst activity during the hydroalkylation was related to the extent of prereduction achieved.

The detrimental effect of too high a water level in the benzene feed was also observed during several cycles of run No. 9 of this example. Thus, in cycle 4 of run No. 9 the catalyst life was significantly reduced compared to cycle 3 when the benzene feed was switched during cycle 4 and it was determined that the new benzene feed which was utilized contained 160 ppm of water whereas the original benzene feed contained 62 ppm of water. However, it can be noted that the catalyst which became deactivated by excess water was capable of regeneration after said deactivation to produce a catalyst with still very excellent activity and selectivity for cyclohexylbenzene. It can be further noted that cycle 5 of run No. 9 was terminated after 192 hours because the desired quantity of cyclohexylbenzene had been obtained and the catalyst was still active after 192 hours.

In cycle 1 shown in Table IV, one example was taken after 19 hours into the cycle. In cycles 2 through 5 shown in Table IV below, two samples were taken; the first sample was taken within a range of 18 to 24 hours after initiation of the cycle and the second sample was taken at the end of the cycle.

Table IV (Run 9)

| Reg Cycle No. | Time, hr Reg[a] | Time Hour on stream[b] | Regeneration[c] Temp °C | Time, hr | Prereduction[d] Temp °C | Time, hr | Reaction, Benzene Temp °C | Conv % | CHB Wt % | Wt Ratio CHB/CH |
|---|---|---|---|---|---|---|---|---|---|---|
| 1 | 37 | 19 | -none- | | -none- | | 183 | 4.8 | 3.5 | 7.8 |
| 2 | 114 | 55 | 440 | 2.0 | -none- | | 183 | 10.0 | 8.1 | 9.5 |
|  |  | 151 |  |  |  |  | 182 | 8.0 | 6.4 | 13.0 |
| 3 | 252 | 170 | 440 | 2.5 | 210–165 | 0.70 | 172 | 11.7 | 9.4 | 8.0 |
|  |  | 403 |  |  |  |  | 174 | 9.4 | 7.5 | 10.0 |
| 4 | 146 | 421 | 435 | 2.0 | 260–200 | 1.5 | 166 | 12.8 | 10.3 | 9.3 |
|  |  | 549 |  |  |  |  | 163 | 9.6 | 7.7 | 7.0 |
| 5 | 192 | 573 | 490 | 2.0 | 238–139 | 1.0 | 178 | 9.7 | 8.1 | 15.0 |
|  |  | 741[e] |  |  |  |  | 180 | 12.7 | 9.2 | 2.8 |

[a]Time between regenerations.
[b]Accumulated time on stream.
[c]In flowing air at atmospheric pressure.
[d]Hydrogen pressure of 3,450 kPa (500 psig).
[e]Recycle benzene containing some cyclohexane was used as feed.

The results of runs 8 and 9 show that the catalyst of the instant invention is capable of producing cyclohexylbenzene from benzene with high selectivity at good conversion rates and at high productivities. The results also demonstrate that the catalyst can be easily regenerated and utilized for extended periods in the hydroalkylation reaction.

What is claimed is:

1. A process for producing monocyclic alkylaromatic hydrocarbons and alkyl-substituted monocyclic alkylaromatic hydrocarbons which comprises contacting a reaction mixture comprising a monocyclic aromatic hydrocarbon or an alkyl-substituted monocyclic aromatic hydrocarbon and hydrogen under hydroalkylation conditions with a catalyst consisting essentially of at least one rhenium compound supported on a calcined, acidic, nickel and rare earth-treated crystalline zeolite selected from the group consisting of type L, type X and type Y zeolites.

2. A process according to claim 1 wherein the rhenium content of the catalyst is within the range of about 0.01 to about 1 percent by weight of said catalyst.

3. A process according to claim 1 wherein the rhenium content of the catalyst is within the range of about 0.05 to about 0.25 percent by weight of said catalyst.

4. A process according to claim 1 wherein the crystalline zeolite is selected from the group consisting of zeolites having a pore diameter within the range of about 7 to about 12 angstroms;
wherein the rare earth metal compounds and the nickel compounds are selected from the group consisting of nitrates, bromides, acetates, chlorides, iodides, sulfates and mixtures of any two or more thereof;
wherein the rare earth metal is selected from the group consisting of cerium, lanthanum, praseodymium, neodymium, samarium, europium, gadolinium, terbium, dysprosium, holmium, erbium, thulium, ytterbium, lutetium and mixtures of any two or more thereof, and
wherein the rhenium compound is selected from the group consisting of perrhenic acid — $HReO_4$, ammonium perrhenate — $NH_4ReO_4$, potassium hexachlororhenate — $K_2ReCl_6$, potassium perrhenate — $KReO_4$, rhenium carbonyl — $Re_2(CO)_{10}$, rhenium heptoxide — $Re_2O_7$, rhenium pentachloride — $ReCl_5$, rhenium trichloride — $ReCl_3$, rhenium trioxide — $ReO_3$, sodium perrhenate — $NaReO_4$ and mixtures of any two or more thereof.

5. A process according to claim 1 wherein the crystalline zeolite is the alkali metal form with the alkali metal content of the calcined, acidic, nickel and rare earth metal-treated crystalline zeolite being within the range of about 0.01 to about 2 percent by weight of said zeolite;
wherein the rare earth metal content of the calcined acidic, nickel and rare earth metal-treated crystalline zeolite is within the range of about 2 to about 25 percent by weight of said zeolite; and
wherein the nickel content of the calcined, acidic, nickel and rare earth metal-treated crystalline zeolite is within the range of about 0.01 to about 15 percent by weight of said zeolite.

6. A process according to claim 1 wherein the crystalline zeolite is the alkali metal form with the alkali metal content of the calcined, acidic, nickel and rare earth metal-treated crystalline zeolite being within the range of about 0.05 to about 1 percent by weight of said zeolite;
wherein the rare earth content of the calcined, acidic, rare earth metal-treated crystalline zeolite is within the range of about 5 to about 20 percent by weight of said zeolite; and
wherein the nickel content of the calcined, acidic, nickel and rare earth metal-treated crystalline zeolite is within the range of about 1 to about 8 percent by weight of said zeolite.

7. A process according to claim 1 wherein the catalyst is treated with hydrogen prior to being contacted with the aromatic hydrocarbon.

8. A process according to claim 1 wherein the aromatic hydrocarbon is benzene which is contacted with said catalyst at a liquid hourly space velocity within the range of about 1 to about 100, a hydrogen pressure within the range of about 690 to about 13,800 kilopascals, a hydrogen feed rate within the range of about 0.1 to about 10 mols per hour of hydrogen per mole of aromatic hydrocarbon per hour, and a temperature within the range of about 100° to about 250° C.

9. A process according to claim 1 wherein the aromatic hydrocarbon is benzene which is contacted with said catalyst at a liquid hourly space velocity within the range of about 5 to about 25, a hydrogen pressure within the range of about 1,380 to about 6,900 kilopascals, a hydrogen feed rate within the range of about 0.2 to about 1 mole of hydrogen per mole of aromatic hydrocarbon per hour, and a temperature within the range of about 140° to about 200° C.

10. A process according to claim 1 wherein the crystalline zeolite is selected from the group consisting of Type X, Type L and Type Y zeolites; and
the rhenium compound is rhenium trichloride, the nickel compound is nickel chloride hexahydrate and the rare earth metal compound is a mixture of the chlorides of at least one of lanthanum, cerium, praseodymium, neodymium, samarium and gadolinium.

* * * * *